United States Patent [19]

Mathys, Jr. et al.

[11] Patent Number: 4,628,920

[45] Date of Patent: Dec. 16, 1986

[54] INTRAMEDULLARY NAIL

[75] Inventors: Robert Mathys, Jr.; Anton Cotting, both of Bettlach, Switzerland

[73] Assignee: Synthes Ltd., Paoli, Pa.

[21] Appl. No.: 717,794

[22] Filed: Mar. 29, 1985

Related U.S. Application Data

[63] Continuation-in-part of Ser. No. 680,515, Dec. 11, 1984, abandoned.

[30] Foreign Application Priority Data

Dec. 12, 1983 [CH] Switzerland .................... 6622/83
May 12, 1984 [EP] European Pat. Off. ....... 84810592.0

[51] Int. Cl.⁴ ............................................. A61F 5/04
[52] U.S. Cl. ............................................. 128/92 YZ
[58] Field of Search .......... 128/92 BC, 92 BA, 92 B, 128/92 BB, 92 R, 92 G

[56] References Cited

U.S. PATENT DOCUMENTS 3,334,624  8/1967  Schneider et al. ................. 128/92
4,462,395  7/1984  Johnson .......................... 128/92 B
4,522,202  6/1985  Otte et al. ....................... 128/92 BC Primary Examiner—Robert P. Swiatek
Assistant Examiner—Cary E. Stone
Attorney, Agent, or Firm—Davis, Hoxie, Faithfull & Hapgood

[57] ABSTRACT

A intramedullary nail of the type adapted to receive a conical drive connection is provided with a slot which extends from the tip to the head for improved elasticity. A locking section is provided at the head to avoid the nail spreading apart when a conical drive connection is used. The nail has a threaded conical socket to receive a drive connection and the thread is shaped to minimize radial forces resulting from driving bolt being screwed into the socket.

11 Claims, 3 Drawing Figures

INTRAMEDULLARY NAIL

This invention relates to intramedullary nails and in particular to an intramedullary nail which is elastic and yet strong enough to be driven in and extracted using a conical drive connection.

A common form of intramedullary nail, the so-called Kuntscher nail, is simply a hollow tube, which may be of triangular cross-section, with rounded corners. A slot is provided in the wall of the tube from one end to the other to provide elasticity or spring, in response to radial compressive forces.

To facilitate the insertion and extraction of intramedullary nails, U.S. Pat. No. 3,334,624 discloses the use of a threaded conical socket at one end of the nail into which a bolt may be inserted. Such nails may also be provided with a longitudinal slot to provide elasticity but in the nail disclosed in U.S. Pat. No. 3,334,624, the slot terminates short of the head of the nail to avoid spreading the nail when a conical bolt is inserted in the socket. With such nails it has been found difficult to insure uniform elasticity over the entire length of the nail.

Experience has shown that it is desirable for the elasticity of intramedullary nails to be as uniform as possible over the length of the nail to avoid any stress concentration at the end of the slot.

In accordance with the present invention high elasticity and strength are achieved in intramedullary nails having driving sockets by providing a slot which extends over the entire length of the nail but which has a section adjacent the head of the nail which has a configuration such as to lock together the edges of the wall of the nail on opposite sides of the slot. Thus the nail is prevented from being spread apart when a conical drive connection is used.

The invention therefore includes an intramedullary nail comprising a hollow body having a peripheral wall, a tip, a head adapted to receive a drive connection, and a slot extending from the tip to the head, said slot having a section adjacent said head with a configuration locking together the edges of the body wall on opposite sides of the slot to prevent spreading of the body.

In a preferred form of the invention the head of the nail is provided with a threaded conical socket for receiving a drive connection. Preferably the inner walls of the socket make an angle of about 2° to about 10° with the axis of the nail and the thread is designed to minimize radial forces on the walls of the socket as the drive connection is inserted in that the side walls of the threads approach normalcy with respect to the axis of the nail.

The invention will be further described with reference to the accompanying drawing in which.

Figure 1:
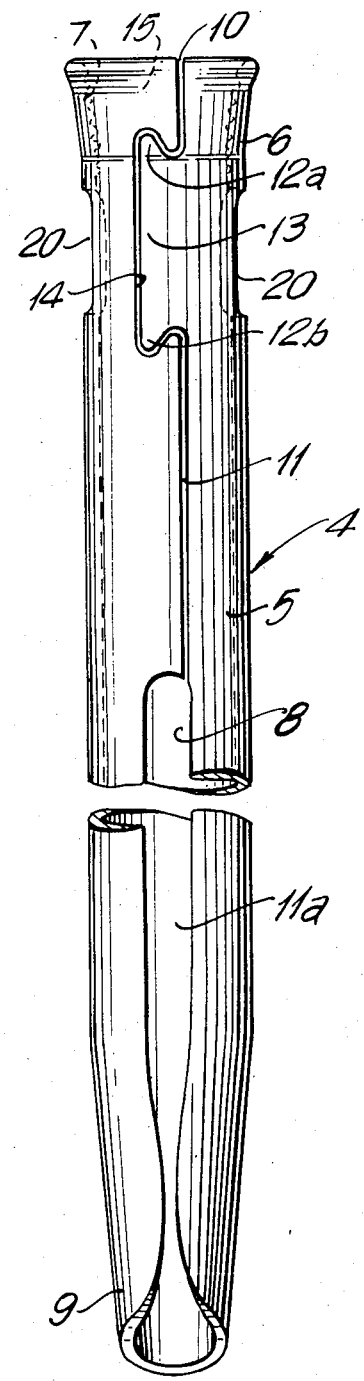
FIG. 1 is a view in front elevation of an intramedullary nail according to the invention, partly broken away.

As shown in FIG. 1, a nail according to the invention comprises a hollow body 4 having a peripheral wall or mantle 5. The wall 5 encloses a hollow space and the nail may have a round cross-section, or a triangular cross-section with the apices of the triangle being rounded. The head 6 of the nail is widened to form a conical socket 15, furnished with an internal thread 7 for receiving a conical bolt (not shown) for inserting and removing the nail. The nail has a slot 8 which, as shown, extends upwardly from the tip 9, to and through the head 6 to the edge 10 of the head. The slot 8, in its upper section 11, is very much narrower than in the lower section 11a and is shaped to lock the edges of the wall 5 on either side of the slot to one another. This locking ability or function is imparted by giving the slot a zigzag, i.e., an S or Z turn, and preferably two such turns, one in the conical part of the head as at 12a and one in the cylindrical part, as at 12b. Thus in FIG. 1 the wall on the right side of the slot has a tongue 13 which fits into a socket 14 formed in the left hand wall, resulting in a dove-tail joint. The tubular nail is thereby prevented from being spread apart or opened up by a conical bolt being screwed tightly down in the socket 15.

The width of the slot in the upper section 11 is subject to some variation. It can be a very narrow fissure in which the edges touch one another. Using laser technology this section of the slot can be made to engage so well that conical bolts can be used in accordance with conventional practice, for driving in and removing the nails with no widening at all of the nail head.

Figure 2:
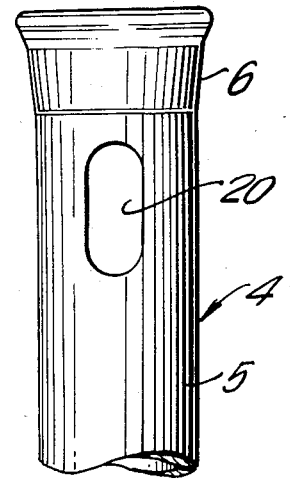
FIG. 2 is a view in side elevation of the upper end of the nail of FIG. 1.

If it is desired to fix the head of the nail, holes 20 (FIG. 2) can be provided for transverse wires or pins (not shown).

Figure 3:
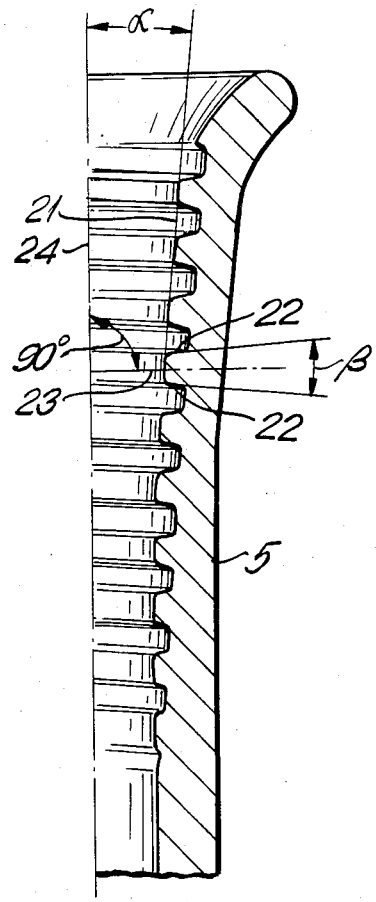
FIG. 3 is an enlarged fragmentary view, partly in vertical section showing details of the preferred form of thread used in an intramedullary nail according to the invention.

Details of the geometry of the threaded socket 15 are shown in FIG. 3. As illustrated, the internal conical wall 21 of the socket is inclined at an angle to the axis 24 of the nail. This angle, $\alpha$, is usually from about 2° to about 10°, preferably about 5°. The thread 7 is designed so that when a bolt is screwed down in the socket, the radial forces acting on the wall 5 are minimized. To achieve this the side walls 22 of the thread make a comparatively small angle with a line 23 drawn normal to the axis of the nail. A convenient design, as shown in FIG. 3, uses a thread which is trapezoidal in cross-section with the included angle $\beta$ being from 0° (i.e., with the side walls 22 of the thread parallel or almost parallel to one another) to about 45°. Preferably $\beta$ is about 10°.

What is claimed:

1. An intramedullary nail comprising a hollow body having a peripheral wall, a tip for insertion into a bone, a head adapted to receive a drive connection and a slot extending from said tip to said head, the slot having a section adjacent said head with a configuration locking together the edges of the body wall on opposite sides thereof to prevent spreading of the body.

2. The nail claimed in claim 1, wherein the configuration of said slot section includes a zig-zag bend.

3. The nail claimed in claim 2 wherein the configuration of said slot section includes two zig-zag bends forming a dove-tailed joint.

4. The nail claimed in claim 1, wherein the head is widened conically and is threaded internally to provide a drive connection and at least a part of said slot section lies in the widened part of said head.

5. The nail claimed in claim 4 wherein the thread is trapezoidal in cross-section with the side walls having an included angle of from 0° to about 45°.

6. The nail claimed in claim 5 wherein the included angle is about 10°.

7. The nail claimed in claim 1, wherein the middle section of the nail is rod shaped in profile and is generally round in cross-section, the section of said slot in which the wall edges are locked together lying at least in part in the rod shaped section of the nail.

8. The nail claimed in claim 1, in which the section of the slot in which the wall eges are locked together is substantially reduced in width compared to the adjacent section of the slot.

9. An intramedullary nail comprising an elongated hollow body having a peripheral wall and a central axis, a tip for insertion into a bone, a head having a threaded conical socket for receiving a drive connection, the internal walls of said socket making an angle between about 2° and 10° with the central axis of the nail, and a slot extending from said tip to said head, the slot having a section adjacent said head with a configuration locking together the edges of the body wall on opposite sides thereof to prevent spreading of the body.

10. The nail claimed in claim 9 wherein the side walls of the thread make a small angle with a line normal to the axis of the nail.

11. The nail claimed in claim 9 wherein the angle is about 5°.

* * * * *